US00PP22835P2

(12) United States Plant Patent
Smith

(10) Patent No.: US PP22,835 P2
(45) Date of Patent: Jul. 3, 2012

(54) *CHRYSANTHEMUM* PLANT NAMED 'SYEDA REDDA'

(50) Latin Name: *Chrysanthemum×morifolium*
Varietal Denomination: Syeda Redda

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/065,206

(22) Filed: Mar. 16, 2011

(51) Int. Cl.
*A01H 5/00* (2006.01)

(52) U.S. Cl. ..... Plt./293

(58) Field of Classification Search ..... Plt./293
See application file for complete search history.

*Primary Examiner* — Annette Para
(74) *Attorney, Agent, or Firm* — Joshua L. Price

(57) ABSTRACT

A new *Chrysanthemum* plant named 'Syeda Redda' particularly distinguished by the medium sized, deep red-purple inflorescences, deep green foliage, round ball-shaped plant habit and a late natural season flowering of about late September.

1 Drawing Sheet

Latin name of the genus and species of the plant claimed: *Chrysanthemum×morifolium.*

Varietal denomination: 'Syeda Redda'.

BACKGROUND OF THE NEW PLANT

The present invention comprises a new *Chrysanthemum*, botanically known as *Chrysanthemum×morifolium*, and hereinafter referred to by the variety name 'Syeda Redda'.

'Syeda Redda' is a product of a planned breeding program. The new cultivar has medium sized, deep red-purple inflorescences, deep green foliage, round ball-shaped plant habit and a late natural season flowering of about late September.

'Syeda Redda' originated from a hybridization made in January 2007 in a controlled breeding environment in Tenjo, Columbia. The female parent was the unpatented, proprietary plant designated '02-M961' with a little larger flower size and red flower color.

The male parent of 'Syeda Redda' was 'Yobonnie', U.S. Plant Pat. No. 18,886, with a smaller plant size, a little more upright habit, and a natural season flowering that is almost three weeks faster. The resultant seed was sown in October 2007.

'Syeda Redda' was selected as one flowering plant within the progeny of the stated cross in the March 2008 in a controlled environment in Alva, Fla.

The first act of asexual reproduction of 'Syeda Redda' was accomplished when vegetative cuttings were propagated from the initial selection in December 2008 in a controlled environment in Alva, Fla.

BRIEF SUMMARY OF INVENTION

Horticultural examination of plants grown from cuttings of the plant initiated in December 2008, and continuing thereafter, has demonstrated that the combination of characteristics as herein disclosed for 'Syeda Redda' are firmly fixed and are retained through successive generations of asexual reproduction.

'Syeda Redda' has not been observed under all possible environmental conditions. The phenotype may vary significantly with variations in environment such as temperature, light intensity and day length.

A Plant Breeder's Right for this cultivar has been applied for in Canada on Mar. 19, 2010 (No. 10-6891). 'Syeda Redda' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syeda Redda' with colors being as true as possible with an illustration of this type.

The photographic drawing shows a flowering potted plant of the new variety.

DETAILED BOTANICAL DESCRIPTION

The plant used for the photographs was about 15 weeks old grown in Monroeville, N.J. in an outdoor trial. One rooted cuttings grown in a nine inch pot with no terminal pinching of the apices. The photograph was taken in mid September 2010 in New Jersey.

The plant descriptions and measurements were taken in Gilroy, Calif. in May 2010 under natural light. Plants were grown under conditions which approximate those generally used for potted *Chrysanthemum* trials in a greenhouse. These plants used in the descriptions were about 10 weeks old.

Color references are made to The Royal Horticultural Society Colour Chart (R.H.S.) 2001.

TABLE 1

DIFFERENCES BETWEEN THE NEW VARIETY 'SYEDA REDDA' AND A SIMILAR VARIETY

| | 'Syeda Redda' | 'Yoregina' (U.S. Plant Pat. No. 14,003) |
|---|---|---|
| Inflorescence size: | Larger | Smaller |
| Plant habit: | More compact/stays rounded in shade | Becomes more upright in shade |
| Foliage coloring: | Stays greener throughout the season | Becomes less green as the season goes on |

Plant:

*Form, growth and habit*.—Herbaceous decorative garden-type, stems upright and outwardly spreading, freely branching, strong and moderately vigorous growth habit.

*Plant height*.—10-12 cm.

*Plant height* (*inflorescence included*).—16-18 cm.

*Plant width*.—25-28 cm.

*Garden performance and tolerance to weather*.—Very good.

Roots:

*Number of days to initiate roots*.—4 days at about 22 degrees C.

*Number of days to produce a rooted cutting*.—10-12 days at 22 degrees C.

*Type*.—Fine, fibrous, free branching.

*Color*.—RHS N155B but whiter.

Foliage:

*Arrangement*.—Alternate.

*Immature, leaf color, upper surface*.—Closest to RHS 139A.

*Lower surface*.—Closest to RHS 137B.

*Mature, leaf color, upper surface*.—Closest to RHS 139A.

*Lower surface*.—Closest to RHS 137B.

*Length*.—4.5-5.0 cm.

*Width*.—3.7-4.2 cm.

*Shape*.—Ovate.

*Base shape*.—Attenuate.

*Apex shape*.—Mucronulate.

*Margin*.—Irregularly lobed; slightly palmate; serrate.

*Texture, upper surface*.—Bifid T-shaped hairs.

*Lower surface*.—Bifid T-shaped hairs.

*Color of veins, upper surface*.—RHS 138B.

*Color of veins, lower surface*.—RHS 138B.

*Petiole color*.—RHS 138B.

*Length*.—1.5 cm.

*Diameter*.—0.1-0.15 cm.

*Texture*.—Bifid T-shaped hairs.

Stem:

*Quantity of main branches per plant*.—7-8.

*Color of stem*.—RHS 137A but appears lighter because of hairs.

*Length of stem*.—10-12 cm.

*Diameter*.—0.2 cm.

*Length of internodes*.—0.5-2.0 cm.

*Texture*.—Bifid T-shaped hairs.

*Color of peduncle*.—RHS 137A but appears lighter.

*Length of peduncle*.—3.3-3.6 cm.

*Peduncle diameter*.—0.1 cm.

*Texture*.—Bifid T-shaped hairs.

Inflorescence:

*Type*.—Compositae type, solitary decorative-type inflorescences, borne terminally above foliage, ray florets arranged acropetally on a capitulum.

*Quantity of short days to flowering* (*response time*).—About 52 days.

*Quantity of inflorescences per plant*.—Approximately 80-85.

*Lastingness of individual blooms on the plant*.—About 5 weeks from the first flower.

*Fragrance*.—Slightly spicy.

Bud (just when opening/showing color):

*Color*.—RHS 187A.

*Length*.—1.0 cm.

*Width*.—0.5-0.6 cm.

*Shape*.—Oblate.

Immature inflorescence:

*Diameter*.—4.0-4.3 cm.

*Color of ray florets, upper surface*.—RHS 187B.

*Lower surface*.—RHS 187D.

Mature inflorescence:

*Diameter*.—5.3-5.6 cm.

*Depth*.—1.0-1.2 cm.

*Total diameter of 'disc'*.—1.1-1.2 cm.

*Receptacle height*.—0.3-0.4 cm.

*Receptacle diameter*.—0.3 cm.

Ray florets:

*Average quantity of florets*.—About 33 in numerous whorls.

*Color of florets, upper surface*.—Closest to RHS 59A but much more velvety red.

*Lower surface*.—RHS 187D.

*Length*.—3.0-3.1 cm.

*Width*.—0.4-0.5 cm.

*Shape*.—Ligulate.

*Apex shape*.—Acute to somewhat irregularly emarginate.

*Margin*.—Entire.

*Texture, upper surface*.—Papillose.

*Lower surface*.—Papillose.

Disc florets:

*Average quantity of florets*.—Approximately 75-100.

*Color of florets*.—RHS 144C basally with RHS 5B at the apex.

*Length*.—0.5 cm.

*Width*.—0.1 cm.

*Shape*.—Tubular, elongated.

*Apex shape*.—Acute, 5 pointed.

Phyllaries:

*Quantity*.—Approximately 25-30.

*Color, upper surface*.—RHS 137C.

*Lower surface*.—RHS 137A.

*Length*.—0.5 cm.

*Width*.—0.2 cm.

*Shape*.—Lanceolate.

*Apex shape*.—Acute.

*Base*.—Fused.

*Margins*.—Entire.

*Texture, upper surface*.—Bifid T-shaped hairs.

*Lower surface*.—Bifid T-shaped hairs.

Reproductive organs:

*Pistil*.—1.

*Length*.—0.5 cm.

*Style color*.—RHS 1C.

*Style length*.—0.4 cm.

*Stigma color*.—RHS 9A.
*Stigma shape*.—Bi-parted.
*Ovary color*.—Not observed.
*Stamens*.—1.
*Color of filaments*.—RHS 1B.
*Length filaments*.—0.2-0.25 cm.
*Anther color*.—RHS 9A.
*Anther length*.—0.1 cm.
*Anther shape*.—Oval to oblong.
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Syeda Redda' substantially as illustrated and described herein.

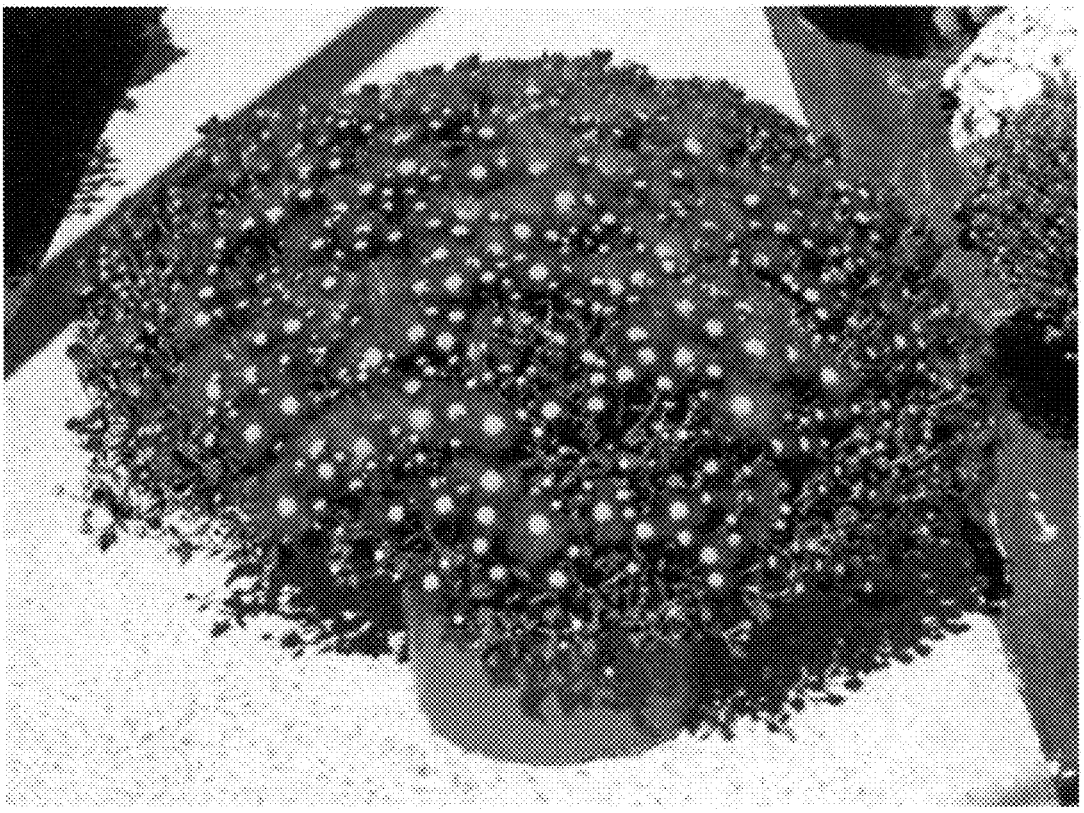

* * * * *